United States Patent
Alkhedhairy et al.

(10) Patent No.: US 9,216,455 B2
(45) Date of Patent: Dec. 22, 2015

(54) METHODS FOR PRODUCING SILVER NANOPARTICLES

(75) Inventors: Abdulaziz A. Alkhedhairy, Riyadh (SA); Javed Musarrat, Riyadh (SA)

(73) Assignees: Abdulaziz A. Alkhedhairy (SA); Javed Musarrat (SA)

( * ) Notice: Subject to any disclaimer, the term of this patent is extended or adjusted under 35 U.S.C. 154(b) by 417 days.

(21) Appl. No.: 12/776,425

(22) Filed: May 10, 2010

(65) Prior Publication Data
US 2011/0274736 A1    Nov. 10, 2011

(51) Int. Cl.
*B22F 9/24* (2006.01)
*C22C 5/06* (2006.01)
*A01N 59/16* (2006.01)

(52) U.S. Cl.
CPC . *B22F 9/24* (2013.01); *A01N 59/16* (2013.01); *C22C 5/06* (2013.01)

(58) Field of Classification Search
None
See application file for complete search history.

(56) References Cited

PUBLICATIONS

Rai et al. Biotechnology Advances 2009 27:76-83.*
Husseiny et al. Spectrochimica Acta Part A 2007 67:1003-1006.*
Denning et al. American Journal of Physiology, Lung, Cellular and Molecular Physiology 2003 285:L584-L592.*
Guzman et al. World Academy of Science, Engineering and Technology 2008 43:357-364.*
Hernandez et al. Applied and Environmental Microbiology 2004 70:921-928.*
Hill et al. Chemistry in Context. 2000 Nelson Thornes Ltd. :Cheltenham p. 193.*
Radziuk et al. Langmuir 2007 23:4612-4617.*
Mussarrat www.dbtbiopesticides.nic.in/index.php?option=com_projects&val=achievements&id=338 2010.*
Pierson et al. Molecular Plant-Microbe Interactions 1992 5:330-339.*
Kemp et al. Nanotechnology 2009 20:1-7.*
Ganesh et al. Journal of Microbiology and Biotechnology 2010 20:1061-1068.*

* cited by examiner

*Primary Examiner* — Robert A Wax
*Assistant Examiner* — Caralynne Helm

(57) ABSTRACT

Methods for producing silver nanoparticles are described. In one aspect, a liquid solution is prepared that contains phenazine-1-carboxylic acid. Silver metal salt is added to the solution to produce multiple silver nanoparticles.

20 Claims, 8 Drawing Sheets
(1 of 8 Drawing Sheet(s) Filed in Color)

METHODS FOR PRODUCING SILVER NANOPARTICLES

BACKGROUND

Silver nanoparticles have a variety of medical and technological applications, such as antibacterial and antifungal agents, semiconductors, and catalysts in chemical reactions. Many existing methods for producing silver nanoparticles are expensive and use harsh chemicals that pose environmental and health risks to individuals responsible for storing and handling the chemicals.

Other existing methods for producing silver nanoparticles require significant time, energy, high-pressure environments, and specialized equipment to complete the production process. The associated risks and expenses, therefore, reduce the commercial feasibility of producing silver nanoparticles using these existing methods.

SUMMARY

The described methods relate to the production of silver nanoparticles. Example methods include preparing a liquid solution containing phenazine-1-carboxylic acid. Silver metal salt is added to the liquid solution, which results in the production of multiple silver nanoparticles when maintained at approximately 28° C. in a dark environment.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the Figures, the left-most digit of a component reference number identifies the particular Figure in which the component first appears.

DETAILED DESCRIPTION

Overview

The methods described herein relate to the production of silver nanoparticles for use in antimicrobial and other applications. These methods produce water-soluble silver nanoparticles that are stable and capable of being stored for six months or longer. The methods discussed herein produce silver nanoparticles in a manner that is less complicated than the existing methods discussed above, and that uses fewer harsh (and environmentally harmful) chemicals than those existing methods. The silver nanoparticles produced according to the procedures discussed herein are useful in a variety of applications, including antimicrobial applications, antifungal applications, semiconductor applications, sensor design applications, silver inks for printable electronic technologies, automotive applications, aerospace applications, nanofilters, nanobiosensors, and catalysts in chemical reactions.

A specific procedure for producing silver nanoparticles uses a redox-active phenazine metabolite combined with silver metal salt. The redox-active phenazine metabolite is a bacterial metabolite obtained by organic extraction of a bacterial culture supernatant. This bacterial metabolite replaces the use of harsh chemicals found in many existing procedures for creating silver nanoparticles. In a particular implementation of the procedure, the redox-active phenazine metabolite is phenazine-1-carboxylic acid (PCA) produced by bacteria Pseudomonas aeruginosa strain NJ-101. The PCA crystals are dissolved in deionized water, to which silver metal salt is added to produce silver nanoparticles. The resulting solution produces silver nanoparticles in a relatively short period of time (e.g., two hours) and is maintained at an ambient temperature. Multiple silver nanoparticles are harvested from the solution, for example, by freeze-drying the solution.

Exemplary Procedures for Producing Silver Nanoparticles

Figure 1:
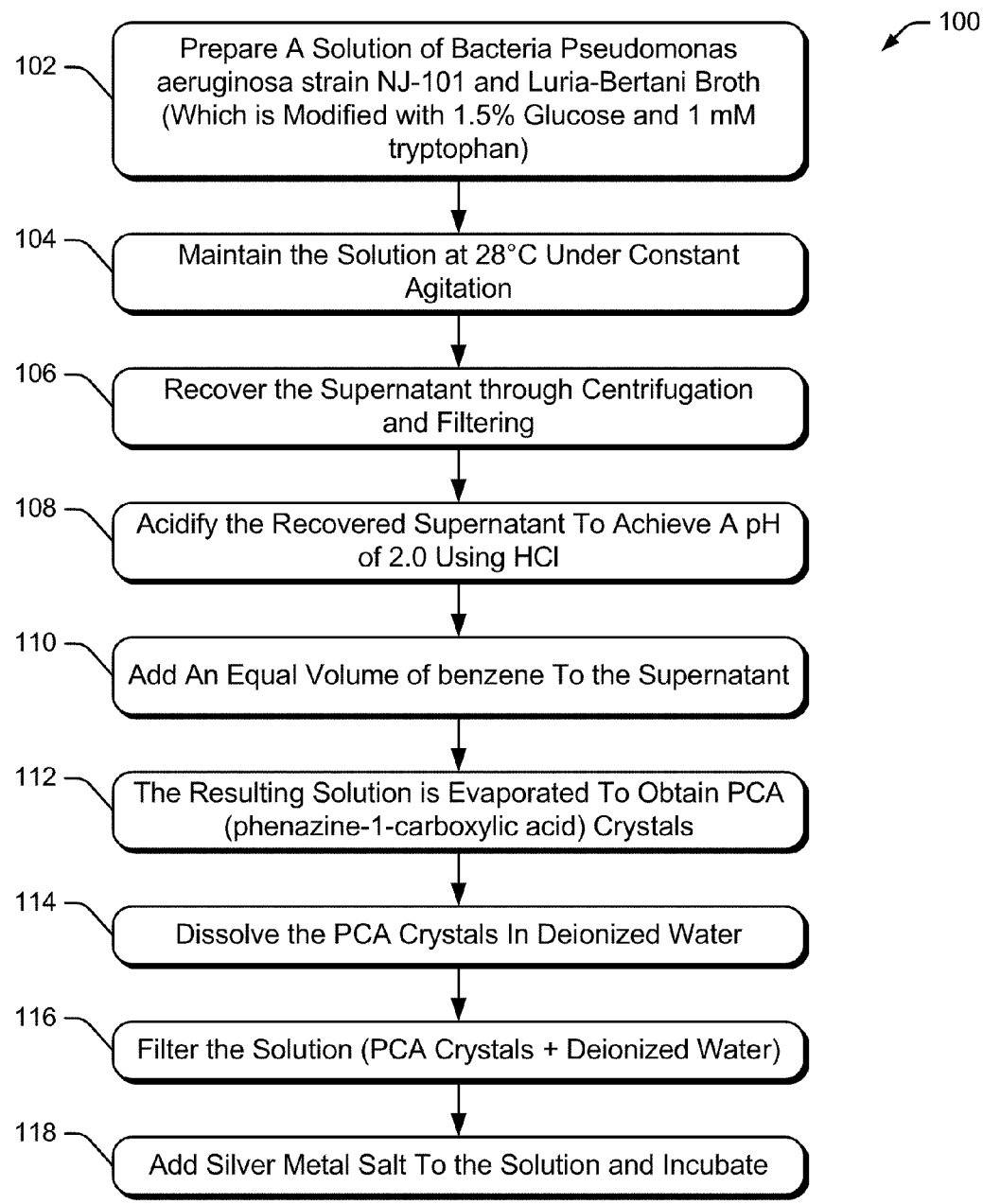
FIG. 1 shows an example procedure for producing silver nanoparticles, according to one embodiment.

FIG. 1 shows an example procedure 100 for producing silver nanoparticles, according to one embodiment. The silver nanoparticles created using this procedure are water-soluble and stable, such that the silver nanoparticles remain stable during storage for at least six months in a colloidal state and for at least a year in a crystalline powdered state.

Procedure 100 begins by preparing a solution of bacteria Pseudomonas aeruginosa strain NJ-101 and Luria-Bertani broth (block 102). Pseudomonas aeruginosa strain NJ-101 is a naturally occurring bacteria. Luria-Bertani broth is a nutritionally rich liquid medium used to grow various types of bacteria. Luria-Bertani broth is also commonly referred to as "Luria broth" or "lysogeny broth". The Luria-Bertani broth is modified with 1.5% glucose and 1 mM tryptophan. Tryptophan is an amino acid that occurs in proteins. The glucose is added to accelerate bacteria growth. The tryptophan is used for feedback inhibition of its own synthesis via Anthranilate synthase I, which facilitates the synthesis of PCA via Anthranilate synthase II pathway using Anthranilate as a substrate. The solution is maintained at a temperature of approximately 28° C. under constant agitation (block 104). In other implementations, the temperature is maintained in the range of approximately 28° C. to 37° C. In a particular embodiment, the solution is maintained at the ambient temperature of a laboratory, production facility, or similar environment, under constant agitation.

The next step in procedure 100 recovers the supernatant from the solution through centrifugation and filtering (block 106). The supernatant is the liquid portion of the solution above the sediment or settled precipitate. In this example, the supernatant exhibits a green color. The centrifugation process is performed at 5000 rpm (revolutions per minute) and the filtering is performed using a 0.45 μm (μm is $10^{-6}$ meters) filter. The recovered supernatant is acidified to achieve a pH of approximately 2.0 using concentrated HCl (hydrogen chloride), block 108. Next, an equal volume of benzene is added to the supernatant (block 110) to create a 1:1 ratio (volume) of benzene to supernatant. In a particular embodiment, the benzene is HPLC (high-performance liquid chromatography) grade benzene. The supernatant and the benzene are mixed thoroughly using a separating funnel. The resulting solution is evaporated to obtain multiple PCA (phenazine-1-carboxylic acid) crystals (block 112). In a particular example, approximately 20 mg (milligrams) of PCA crystals are produced from a supernatant having a volume of approximately 500 ml (milliliters).

The PCA crystals produced from the evaporation process are dissolved in deionized water (block 114). In the above example of approximately 20 mg of PCA crystals, the PCA crystals are dissolved in approximately 100 μl (μl is $10^{-6}$ liters) of deionized water. The solution of PCA crystals and deionized water then is filtered (block 116) through a 0.45 μm filter. Finally, silver metal salt is added to the solution and incubated (block 118) for a period of approximately two hours at a temperature of approximately 28° C. In a particular implementation, the solution is incubated in a dark environment. A quantity of silver metal salt is added to the solution to produce a silver metal salt concentration of $10^{-3}$ M (also referred to as "1 mM") in the solution. In one embodiment of procedure 100, the silver metal salt added to the solution is $AgNO_3$. The PCA in the solution with the silver nanoparticles acts as a stabilizer for the silver nanoparticles by providing electrostatic and steric repulsion. The stabilization provided by the PCA prevents the nanoparticles from combining with each other to form aggregates, which could continue to grow and gradually settle out of suspension.

The described procedure provides an efficient biological system for the in vitro synthesis of stable and dispersible silver nanoparticles. The procedure is environmentally friendly and can be scaled upwards for commercial applications. Using the described procedure, approximately 18 mg to 20 mg of PCA is produced by a 500 ml culture, which produces approximately 160 mg of silver nanoparticles per liter of 1 mM $AgNO_3$ solution. The average size of silver nanoparticles produced using the procedures described herein is 10 nm to 38 nm (nanometers).

In another embodiment, a different phenazine derivative, phenazine-1-carboxamide (PCN) is used in place of PCA. In this embodiment, the PCN is extracted from bacterial strain *Pseudomonas aeruginosa* strain NJ-101. In this embodiment, the average size of silver nanoparticles produced is 14 nm to 39 nm.

Figure 2:
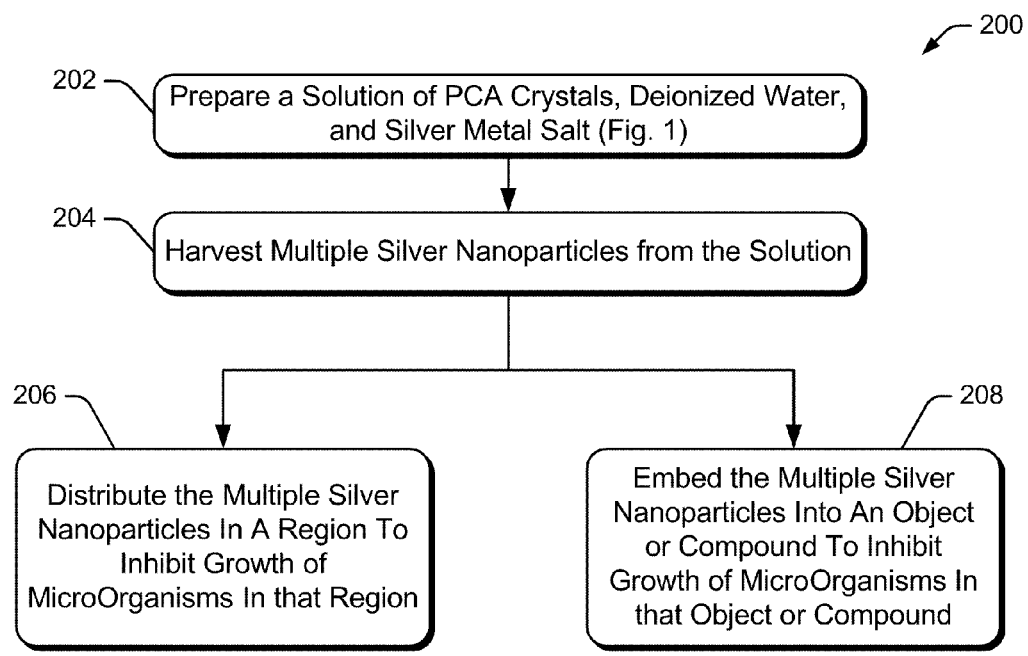
FIG. 2 shows an example procedure for inhibiting microorganism growth, according to one embodiment.

FIG. 2 shows an example procedure 200 for inhibiting microorganism growth, according to one embodiment. This procedure begins by preparing a solution of PCA crystals, deionized water, and silver metal salt (block 202), as discussed above with respect to FIG. 1. Multiple silver nanoparticles are harvested from that solution (block 204) by freeze-drying the solution. The harvested silver nanoparticles are capable of inhibiting microorganism growth (e.g., inhibiting growth of bacteria or fungus) in a variety of environments. In one application, multiple silver nanoparticles are distributed in a particular region to inhibit growth of microorganisms in that region (block 206). For example, silver nanoparticles applied to a medical bandage can inhibit growth of microorganisms on the surface of the medical bandage and any areas that come in contact with the bandage. A particular region may be of any size and shape, and may include a surface, an object, a compound, or other element.

In another application, multiple silver nanoparticles are embedded into an object or compound to inhibit growth of microorganisms in (or upon) that object or compound (block 208). For example, silver nanoparticles embedded into a medical instrument or storage container can inhibit the growth of microorganisms on the surface of the medical instrument or in the storage container.

The silver nanoparticles produced according to the procedures discussed herein are effective antimicrobials for inhibiting the growth of various bacterial and fungal strains, such as *Shigella, Streptococcus aureus, Citrobactor, Escherichia coli, Pseudomonas aeruginosa, Bacillus subtilis, Candida albicans*, and *Fusarium oxysporum*.

As discussed above, FIG. 2 shows an embodiment of a procedure for inhibiting microorganism growth using silver nanoparticles. Alternate uses of silver nanoparticles may utilize similar procedures to harvest and distribute (or otherwise apply) silver nanoparticles in a variety of applications. Additionally, harvested silver nanoparticles can be stored for a variety of future uses. The silver nanoparticles produced using the procedures discussed herein remain stable during storage for at least six months in a colloidal state and for at least a year in a crystalline powdered state.

Figure 3:
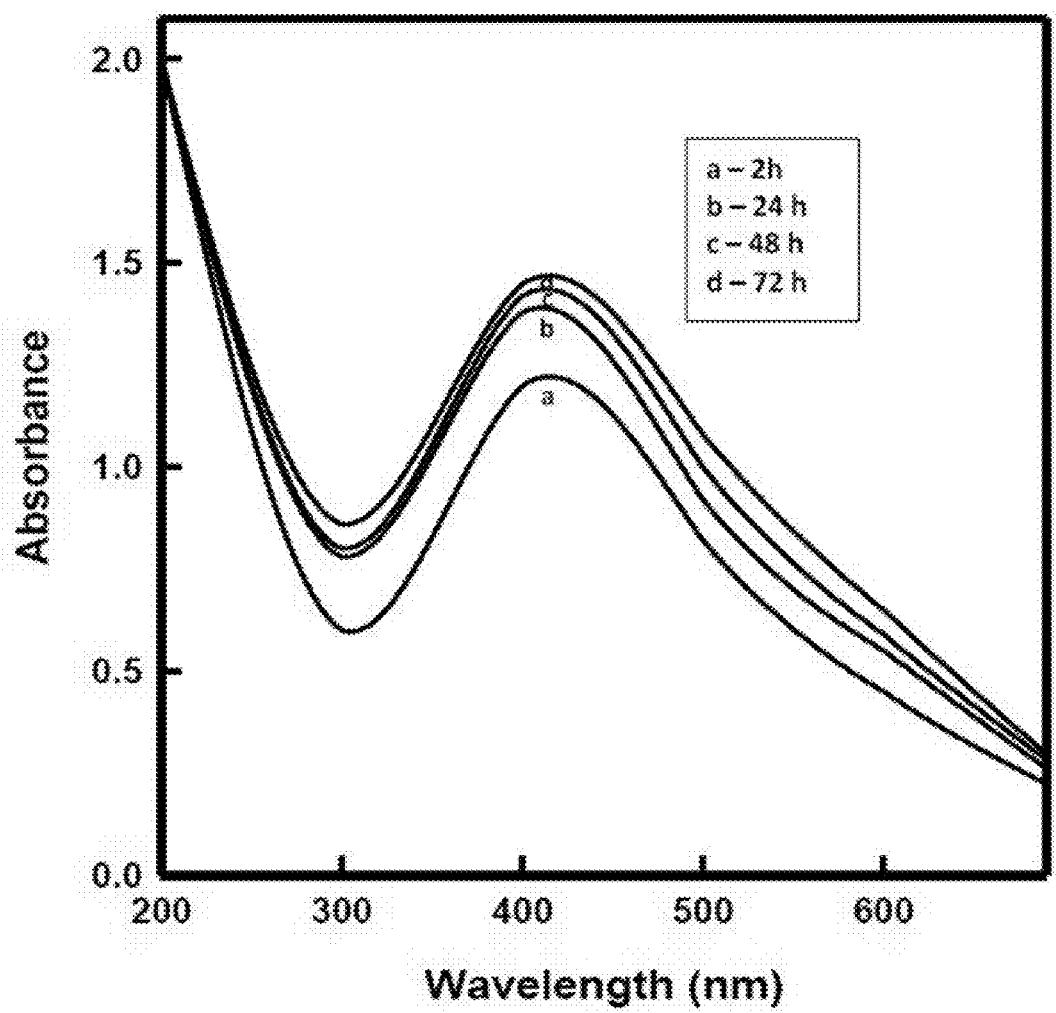
FIG. 3 shows an example UV-Visible absorption spectra for silver nanoparticles produced according to the procedure of FIG. 1.

FIG. 3 shows an example UV-Visible absorption spectra for silver nanoparticles produced according to the procedure of FIG. 1. The graph shown in FIG. 3 depicts the growth of the surface plasmon resonance (SPR) peak of silver nanoparticles with time-dependent reduction of silver metal ions. In FIG. 3, line a represents approximately two hours, line b represents approximately 24 hours, line c represents approximately 48 hours, and line d represents approximately 72 hours. The SPR is an important property of certain silver nanoparticles, by reflecting the frequency at which conduction electrons oscillate and scatter/absorb the incident electromagnetic waves. Metals such as Au, Ag, Cu, and alkaline metals, with free conduction electrons, have plasmon resonance in the visible spectrum. The enhancement of the SPR peaks (as shown in FIG. 3) with increased reaction time suggests an increase in the number of nanoparticles produced over time.

Figure 4:
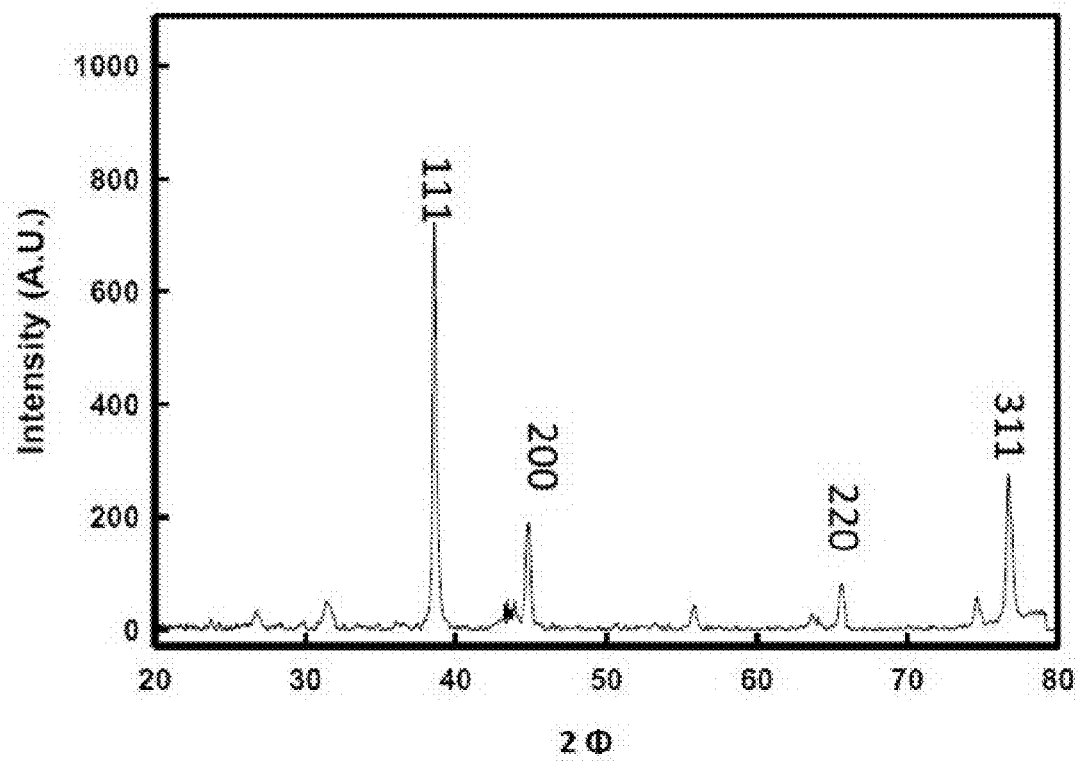
FIG. 4 shows an example pattern representing the crystalline nature of the silver nanoparticles produced according to the procedure of FIG. 1.

FIG. 4 shows an example pattern representing the crystalline nature of the silver nanoparticles, according to one embodiment. The silver nanoparticles produced according to the procedures discussed herein were analyzed using $CuK_\alpha$ radiation (λ=1.54056 Å) in the range of 20°≤2θ≤80° at 40 keV. A single absorption peak at 420 nm and sharp X-ray diffraction (XRD) bands (as shown in FIG. 4) confirm the formation of silver nanoparticles in single-phase hexagonal crystal symmetry. In this example, the particle size is estimated using the Scherrer equation D=0.9 λ/B Cos θ, where λ is the wavelength of the X-ray, B is the broadening of the diffraction line measured at half of its maximum intensity in radians, and θ is the Bragg's diffraction angle. The diffractions at 38.5°, 44°, 64.5°, and 72° can be indexed to the (111), (200), (220), and (311) planes of the face-centered cubic (fcc) silver, respectively. The XRD pattern indicates that the silver nanoparticles formed by the reduction of Ag+ ions are crystalline in nature. The particle size is estimated to be approximately 32 nm, based on the line width of the (111) XRD peak.

Figure 5:
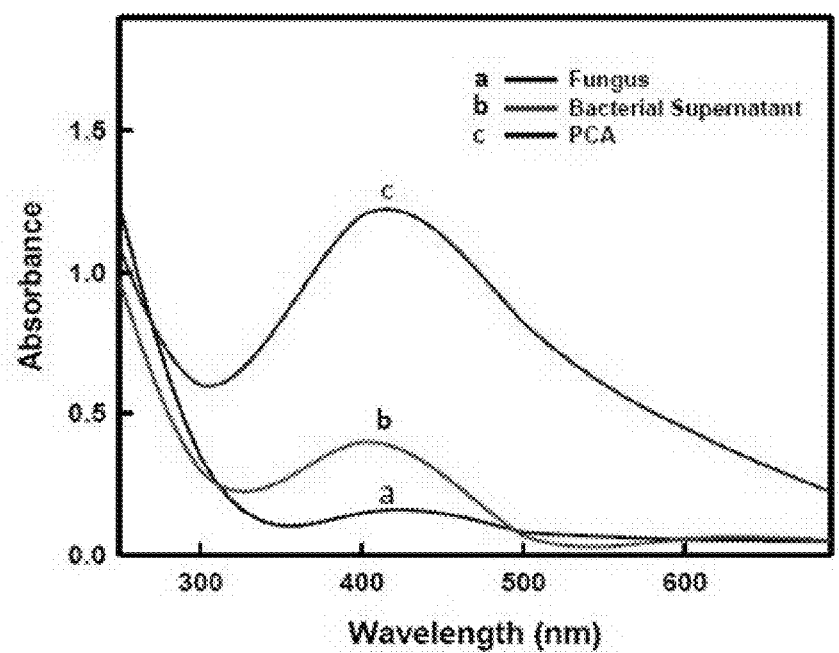
FIG. 5 shows example efficiencies of various methods of producing silver nanoparticles.

FIG. 5 shows example efficiencies of various methods for producing silver nanoparticles. As illustrated in FIG. 5, the efficiency of producing silver nanoparticles with PCA (line c) is significantly better than the fungal (line a) and bacterial (line b) extracts based on the SPR peak intensity at 420 nm, which indicates the amount of silver nanoparticles. The transmission electron microscopy (TEM) analysis of PCA-based silver nanoparticles was performed by drop-coating of the nanoparticles solution on carbon-coated copper TEM grids (40 μm×40 μm mesh size). TEM measurements were performed using an electron microscope operated at an accelerating voltage of 100 kV. A representative TEM image recorded from the silver nanoparticle film deposited on a carbon-coated copper TEM grid is shown in FIG. 6.

Figure 6:
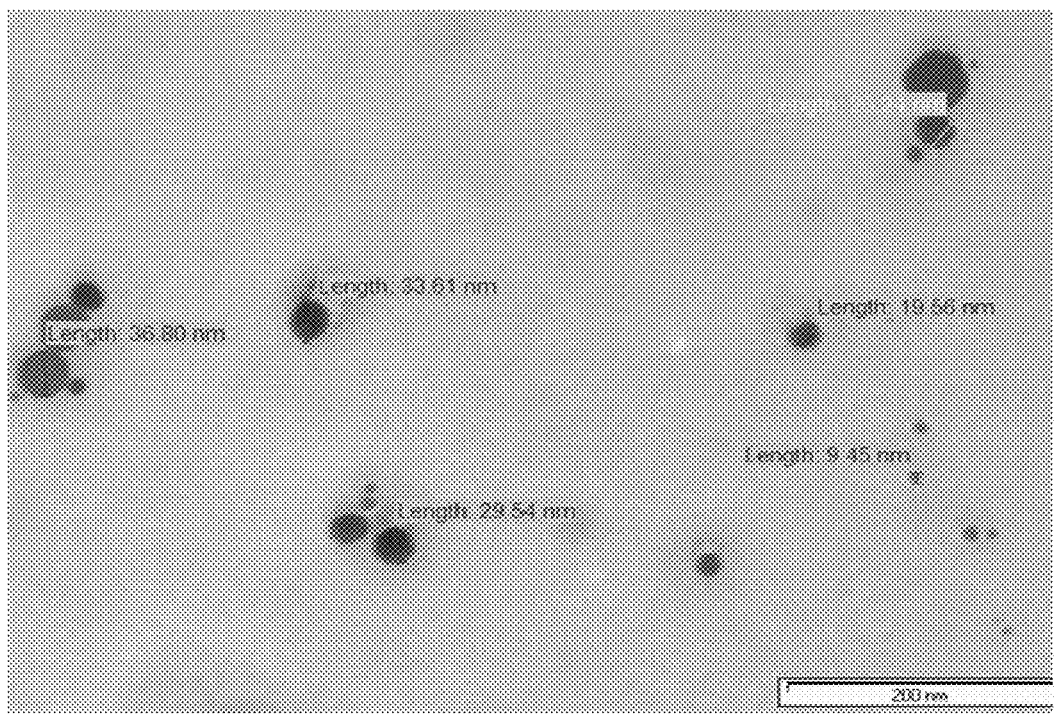
FIG. 6 shows multiple silver nanoparticles produced according to the procedure of FIG. 1.

The image of FIG. 6 shows the individual silver nanoparticles of varying morphology in the size range of 9.5 nm to 36.8 nm. The silver nanoparticles shown in FIG. 6 appear to be monodispersed with no significant aggregation, which indicates the stability of the silver nanoparticles upon interaction with PCA. This is consistent with the UV-Visible spectroscopy measurements shown in FIGS. 3 and 5, and reaffirms the characteristic of well-dispersed silver nanoparticles resulting from the procedures discussed herein.

The silver nanoparticles were also examined using an atomic force microscope (AFM) running in non-contact tapping mode. Characterization was performed by observing patterns on the surface topography and by studying data provided by the AFM. Tapping mode imaging was implemented in ambient air by oscillating the cantilever assembly at or near the cantilever's resonant frequency using a piezoelectric crystal. The topographical images were obtained in tapping mode at a resonance frequency of 218 kHz. The average size of the silver nanoparticles was determined to be 38 nm, based on use of the "WSxM" software application. The WSxM application performs data acquisition and processing in scanning probe microscopy (SPM), and is available from Nanotec Electronica S.L. in Madrid, Spain.

Figure 7:
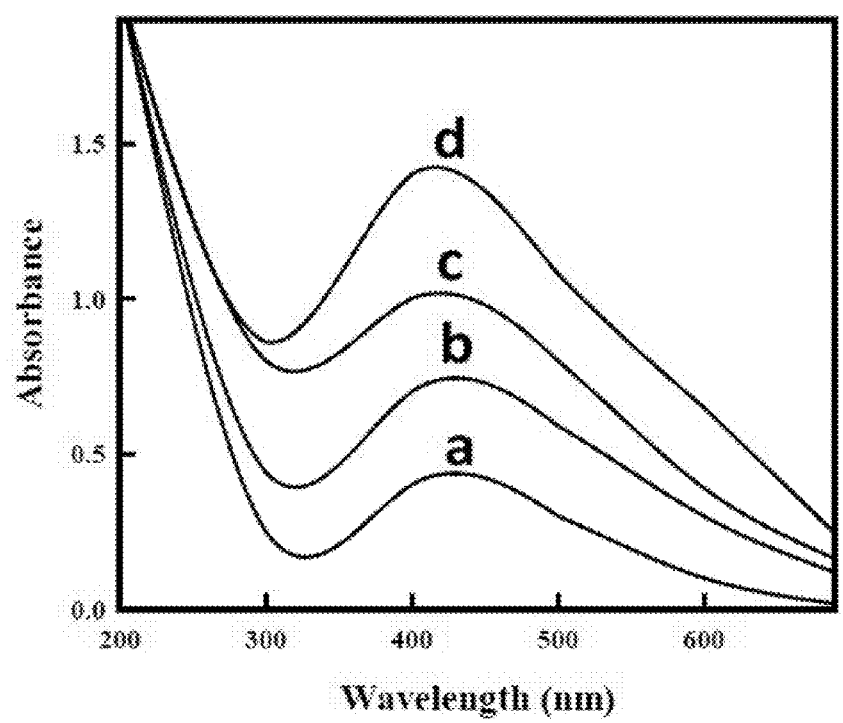
FIG. 7 shows an example UV-Visible absorption spectra for silver nanoparticles produced by phenazine-1-carboxamide.

FIG. 7 shows an example UV-Visible absorption spectra for silver nanoparticles produced by phenazine-1-carboxamide (PCN) instead of PCA. The lines shown in FIG. 7 represent time of incubation: line a is approximately 15 minutes, line b is approximately 30 minutes, line c is approximately one hour, and line d is approximately two hours.

Figure 8:
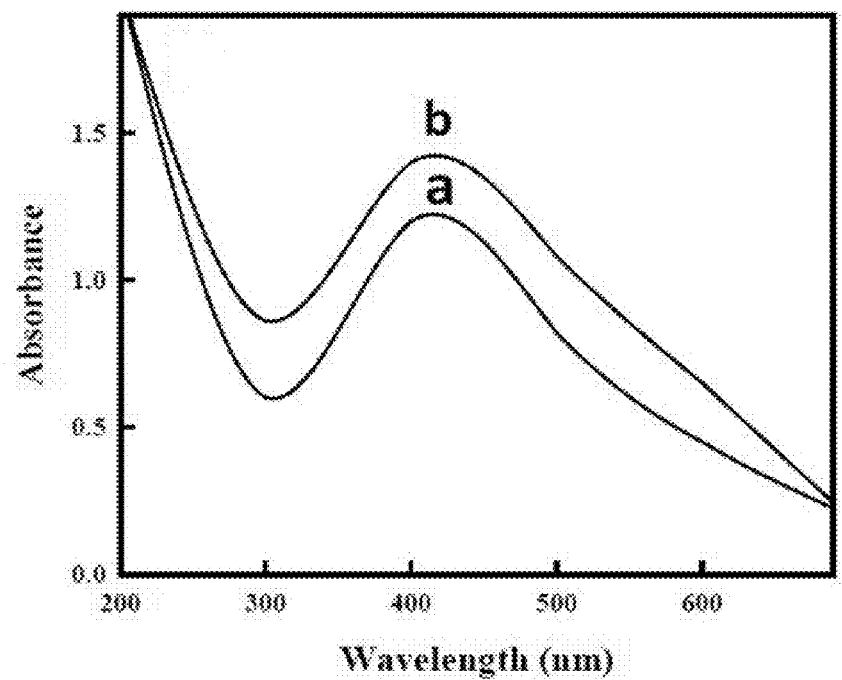
FIG. 8 shows an example comparison of the production of silver nanoparticles using phenazine-1-carboxylic acid (line a) and phenazine-1-carboxamide (line b).

FIG. 8 shows an example comparison of the production of silver nanoparticles using PCA (line a) and PCN (line b). As shown in FIG. 8, PCN produces slightly more silver nanoparticles than methods using PCA. The comparison shown in this figure represents silver nanoparticle production after approximately two hours of incubation.

Example 1

This example produces silver nanoparticles in an aqueous medium using phenazine-1-carboxylic acid (PCA) produced by bacteria *Pseudomonas aeruginosa* strain NJ-101. The bacteria were maintained on nutrient agar slants. Upon achieving bacterial growth in Luria-Bertani broth (pH 7.2) at 37° C. for 18 hours, the slants were prepared and preserved at 10° C., and cryopreserved as glycerol cultures at −20° C.

Starting material was obtained from late log phase cultures after 24 hours of incubation at 28° C. Bacterial biomass was grown in a 1000 ml Erlenmeyer flask containing 500 ml of Luria-Bertani broth (pH 7.2+/−0.2), modified with 1.5% glucose and 1 mM tryptophan. The bacterial biomass was maintained at 28° C. and constantly agitated on a rotary shaker at 200 rpm for 48 hours. The bacterial biomass was separated from the culture broth at different time periods by centrifugation at 5000 rpm for 10 minutes at 20° C. The supernatant (500 ml) was acidified with concentrated HCl to achieve a pH of 2.0. HPLC grade benzene was added in the volume ratio of 1:1 and mixed thoroughly. The mixture then was centrifuged at 5000 rpm for 15 minutes. The top organic phase was pooled and evaporated to dryness.

The dried yellow extracted material was dissolved in deionized Milli Q water to obtain a yellow colored PCA solution. Addition of 100 μl of PCA solution to 100 ml of 1 mM AgNO$_3$ solution in a 500 ml Erlenmeyer flask resulted in a color change from yellow to reddish-brown, which is indicative of instant silver nanoparticle synthesis. The reaction was relatively fast during the first two hours, then gradually slowed and attained equilibrium after 72 hours.

The redox potential of the PCA was assessed using cyclic voltametry. At regular time points, aliquots of 1 ml were collected and monitored for Surface Plasmon Resonance of silver nanoparticles. The reddish-brown aqueous solution was freeze-dried, and the resulting powder of silver nanoparticles was stored at room temperature. The powder samples were analyzed by UV-Visible spectophotometry, X-ray diffraction (XRD), transmission electron microscopy (TEM), and atomic force microscopy.

Example 2

This example produces silver nanoparticles in an aqueous medium using phenazine-1-carboxylic acid (PCA) produced by bacteria *Pseudomonas aeruginosa* strain NJ-101. This example used bacterial culturing similar to Example 1, discussed above. Bacterial biomass is grown in a 500 ml Erlenmeyer flask containing 100 ml of Luria broth with continuous shaking on a rotary shaker at 200 rpm for 48 hours at 28° C. The biomass was separated from the culture broth by centrifugation at 3000 rpm for 10 minutes at 20° C. The supernatant (100 ml) was treated with a 1 mM AgNO$_3$ solution in a 500 ml Erlenmeyer flask for 72 hours with constant stirring.

The color of the aqueous medium changed from pale yellow to reddish-brown after two hours, and the color intensity increased for a time period up to 72 hours. At regular time points, aliquots of 1 ml were collected and monitored for Surface Plasmon Resonance of silver nanoparticles. After 48 hours, the reddish-brown aqueous solution was freeze-dried, and the resulting powder of silver nanoparticles was stored at room temperature. The powder samples were analyzed by X-ray diffraction (XRD), transmission electron microscopy (TEM), and atomic force microscopy. The antimicrobial activity was determined at neutral pH using the agar diffusion method.

CONCLUSION

Although the methods for producing silver nanoparticles have been described in language specific to structural features and/or methodological operations or actions, it is understood that the implementations defined in the appended claims are not necessarily limited to the specific features or actions described. Rather, the specific features and operations of producing silver nanoparticles are disclosed as exemplary forms of implementing the claimed subject matter.

The invention claimed is:

1. A method of producing silver nanoparticles, the method comprising:
    preparing a liquid solution containing phenazine-1-carboxylic acid in an amount having a ratio of 20 mg of phenazine-1-carboxylic acid to 100 μl of the liquid solution; and
    adding a silver metal salt to the liquid solution in a concentration of 1 mM of the silver metal salt to the liquid solution so as to produce silver nanoparticles.
2. A method as recited in claim 1 further comprising incubating the combined silver metal salt and liquid solution for approximately two hours at approximately 28° C.

3. A method as recited in claim 1 further comprising incubating the combined silver metal salt and liquid solution at approximately 28° C. in a dark environment.

4. A method as recited in claim 1 wherein the silver metal salt is $AgNO_3$.

5. A method as recited in claim 1 wherein preparing the liquid solution includes:
- preparing a first solution of bacteria *Pseudomonas aeruginosa* strain NJ-101 and Luria-Bertani broth;
- recovering the supernatant from the first solution;
- acidifying the supernatant;
- adding benzene to the supernatant;
- evaporating the supernatant to obtain phenazine-1-carboxylic acid crystals; and
- dissolving the phenazine-1-carboxylic acid crystals in deionized water.

6. A method as recited in claim 5 further comprising filtering the solution of phenazine-1-carboxylic acid crystals and deionized water.

7. A method as recited in claim 1 further comprising freeze-drying the liquid solution to harvest the plurality of silver nanoparticles.

8. A method as recited in claim 1 wherein the method is performed at an ambient temperature.

9. A method as recited in claim 1 wherein the silver nanoparticles are water-soluble silver nanoparticles.

10. A method of producing silver nanoparticles, the method comprising:
- preparing a liquid solution containing a redox-active phenazine metabolite in an amount having a ratio of 20 mg of redox-active phenazine metabolite to 100 µl of the liquid solution;
- adding a silver metal salt to the liquid solution in a concentration of 1 mM of the silver metal salt to the liquid solution; and
- incubating the liquid solution at an ambient temperature to produce a plurality of silver nanoparticles.

11. A method as recited in claim 10 wherein the redox-active phenazine metabolite is phenazine-1-carboxylic acid.

12. A method as recited in claim 10 wherein the redox-active phenazine metabolite is phenazine-1-carboxamide.

13. A method as recited in claim 10 wherein the redox-active phenazine metabolite is produced from a bacteria.

14. A method as recited in claim 13 wherein the bacteria is *Pseudomonas aeruginosa* strain NJ-101.

15. A method as recited in claim 10 further comprising freeze-drying the liquid solution to harvest the plurality of silver nanoparticles.

16. A method of inhibiting microorganism growth, the method comprising:
- preparing a liquid solution containing phenazine-1-carboxylic acid in an amount having a ratio of 20 mg of phenazine-1-carboxylic acid to 100 µl of the liquid solution;
- adding a silver metal salt to the liquid solution in a concentration of 1 mM of the silver metal salt to the liquid solution so as to produce silver nanoparticles;
- harvesting the silver nanoparticles; and
- distributing at least a portion of the harvested silver nanoparticles in a region to inhibit microorganism growth in that region.

17. A method as recited in claim 16 wherein distributing at least a portion of the harvested silver nanoparticles includes embedding silver nanoparticles into an object.

18. A method as recited in claim 1 wherein the liquid solution has a volume of 100 µl, and wherein the phenazine-1-carboxylic acid has a mass of 20 mg.

19. A method as recited in claim 10 wherein the liquid solution has a volume of 100 µl, and wherein the redox-active phenazine metabolite has a mass of 20 mg.

20. A method as recited in claim 16 wherein the liquid solution has a volume of 100 µl, and wherein the phenazine-1-carboxylic acid has a mass of 20 mg.

* * * * *